United States Patent [19]

Satake

[11] Patent Number: 5,939,434
[45] Date of Patent: Aug. 17, 1999

[54] TETRAZOLYL-SUBSTITUTED QUINUCLIDINES AS SUBSTANCE P ANTAGONISTS

[76] Inventor: Kunio Satake, Pfizer Inc, 235 E. 42nd St., New York, N.Y. 10017-5755

[21] Appl. No.: 08/924,171

[22] Filed: Sep. 5, 1997

[30] Foreign Application Priority Data

Sep. 12, 1996 [WO] WIPO ............ PCT/IB96/00934

[51] Int. Cl.⁶ .......... A61K 31/44; C07D 453/02
[52] U.S. Cl. .......... 514/305; 546/133; 546/137
[58] Field of Search ............ 546/133, 137; 514/305

[56] References Cited

U.S. PATENT DOCUMENTS

| | | | |
|---|---|---|---|
| 4,680,283 | 7/1987 | Veber et al. | 514/17 |
| 5,242,930 | 9/1993 | Baker et al. | 514/305 |
| 5,288,730 | 2/1994 | Baker et al. | 514/305 |
| 5,538,982 | 7/1996 | Hagen et al. | 514/305 |
| 5,569,662 | 10/1996 | Satake et al. | 514/305 |
| 5,604,241 | 2/1997 | Ito et al. | 514/305 |
| 5,716,965 | 2/1998 | Ito et al. | 514/305 |
| 5,741,797 | 4/1998 | Satake | 514/305 |

FOREIGN PATENT DOCUMENTS

| | | |
|---|---|---|
| 0499313 | 8/1992 | European Pat. Off. . |
| WO9005729 | 5/1990 | WIPO . |
| WO9220676 | 11/1992 | WIPO . |
| WO9319064 | 9/1993 | WIPO . |
| WO9410170 | 5/1994 | WIPO . |
| WO9426740 | 11/1994 | WIPO . |
| WO9502595 | 1/1995 | WIPO . |
| WO9508549 | 3/1995 | WIPO . |

OTHER PUBLICATIONS

C.J. Swain et al., in the *Journal of Medicinal Chemistry*, vol. 38,. No. 24, pp. 4793–4805 (1995).
P. Ward et al., in the *Journal of Medicinal Chemistry*, vol. 38, No. 26, pp. 4985–4992 (1995).
E.J. Warawa et al., in the *Journal of Medicinal Chemistry*, vol. 17, No. 5, p. 497 (1974).
S. R. Wilson et al., in the *Journal of the American Chemical Society*, vol. 102, No. 10, p. 3577 (1980).
D. G. Payan et al., in the *Journal of Immunology*, vol. 133, p. 3260 (1984).
I. J. Reynolds et al., in the *Journal of Pharmacology and Experimental Therapeutics*, vol. 237, p. 731 (1986).
A. Nagahisa et al., in the *European Journal of Pharmacology*, vol. 217, pp. 191–195 (1992).
C.J. Swain et al., in the *Bioorganic and Chemistry Letters*, vol. 3, No. 8, pp. 1703–1706, (1993).
D.R. Armour et al., in *Bioorganic and Medicinal Chemistry Letters*, vol. 6, No. 9, pp. 1015–1020 (1996).
C.C. Eschenfelder et al., in the *European Journal of Neuroscience*, vol. 7, pp. 1520–1526 (1995).

*Primary Examiner*—Mukund J. Shah
*Assistant Examiner*—Brenda Coleman
*Attorney, Agent, or Firm*—Dr.Peter C. Richardson; Dr.Paul H. Ginsburg; Kenneth B. Rubin

[57] ABSTRACT

This invention provides a compound of the formula:

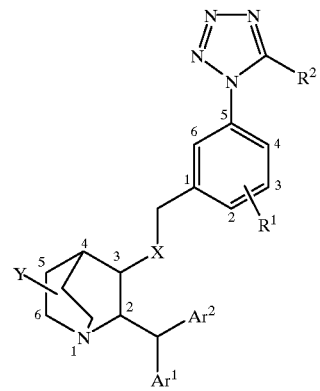

(I)

and its pharmaceutically acceptable salts, wherein $R^1$ is halo, $C_1-C_6$ alkyl, halo $C_1-C_6$ alkyl, $C_1-C_6$ alkoxy or halo $C_1-C_6$ alkoxy; $R^2$ is hydrogen, $C_1-C_6$ alkyl, halo $C_1-C_6$ alkyl, $C_1-C_6$ alkyl-S-, $C_1-C_6$ alkyl-SO—, $C_1-C_6$ alkyl-SO$_2$—, cyclopropyl, phenyl, —NH$_2$, —NH(CH$_3$), —NHC(=O)CH$_3$, —N(CH$_3$)$_2$, —N(C$_2$H$_5$)$_2$ or —CH$_2$C(=O)CF$_3$; $Ar^1$ and $Ar^2$ are independently phenyl, halophenyl or thienyl; X is NH, O or S; and Y is hydrogen, —COOR$^3$ or —CONR$^4$R$^5$, wherein $R^3$, $R^4$ and $R^5$ are independently hydrogen or $C_1-C_6$ alkyl. These compounds are useful as analgesics or anti-inflammatory agents, or in the treatment of allergic disorders, angiogenesis, CNS disorders, emesis, gastrointestinal disorders, sunburn, urinary incontinence, or diseases, disorders or adverse conditions caused by *Helicobacter pylori*, or the like, in a mammalian subject, especially human, especially as analgesics or anti-inflammatory agents in the periphery.

15 Claims, No Drawings

TETRAZOLYL-SUBSTITUTED QUINUCLIDINES AS SUBSTANCE P ANTAGONISTS

TECHNICAL FIELD

This invention relates to novel tetrazolyl-substituted quinuclidine compounds and their pharmaceutically acceptable salts, pharmaceutical compositions containing such compounds, and the use of such compounds as substance P antagonists.

BACKGROUND ART

Substance P is a naturally occurring undecapeptide belonging to the tachykinin family of peptides, the latter being so-named because of their prompt stimulatory action on smooth muscle tissue. More specifically, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine, as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc. It is also reported that the tachykinin antagonists are useful for the treatment of allergic conditions, immunoregulation, vasodilation, bronchospasm, reflex or neuronal control of the viscera and senile dementia of the Alzheimer type, emesis, sunburn and *Helicobacter pylori* infection.

International Publications WO92/20676, WO94/10170 and WO94/26740 disclose a wide variety of substituted benzylaminoquinuclidine derivatives. WO95/02595 and European Patent Publication EP,0,499,313A1 disclose a wide variety of substituted benzyloxy quinuclidine derivatives. WO95/08549 discloses tetrazolylbenzylamino derivatives, as antagonists of tachykinin such as substance P.

BRIEF DESCRIPTION OF THE INVENTION

The present invention provides tetrazolyl-substituted quinuclidine compounds of the following chemical formula (I):

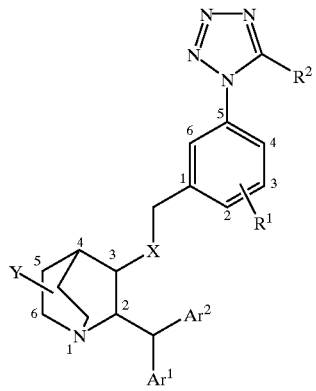

(I)

and its pharmaceutically acceptable salts, wherein
$R^1$ is halo, $C_1$–$C_6$ alkyl, halo $C_1$–$C_6$ alkyl, $C_1$–$C_6$ alkoxy or halo $C_1$–$C_6$ alkoxy;

$R^2$ is hydrogen, $C_1$–$C_6$ alkyl, halo $C_1$–$C_6$ alkyl, $C_1$–$C_6$ alkyl-S—, $C_1$–$C_6$ alkyl-SO—, $C_1$–$C_6$ alkyl-SO$_2$—, cyclopropyl, phenyl, —NH$_2$, —NH(CH$_3$), —NHC(=O)CH$_3$, —N(CH$_3$)$_2$, —N(C$_2$H$_5$)$_2$ or —CH$_2$C(=O)CF$_3$;

$Ar^1$ and $Ar^2$ are independently phenyl, halophenyl or thienyl;

X is NH, O or S; and

Y is hydrogen, —COOR$^3$ or —CONR$^4$R$^5$, wherein $R^3$, $R^4$ and $R^5$ are independently hydrogen or $C_1$–$C_6$ alkyl.

These compounds are useful as substance P antagonists, and thus useful as analgesics or anti-inflammatory agents, or in the treatment of allergic disorders, angiogenesis, central nervous system (CNS) disorders, emesis, gastrointestinal disorders, sunburn, urinary incontinence, and diseases, disorders and adverse conditions caused by *Helicobacter pylori*, or the like, in a mammalian subject, especially human. These compounds are especially useful as analgesics or anti-inflammatory agents in the periphery of the subject.

Accordingly, the present invention provides a pharmaceutical composition for the prevention or treatment of a medical condition for which substance P receptor antagonist activity is needed, in a mammalian subject, which comprises the compound of the formula (I) or a pharmaceutically acceptable salt thereof, and a pharmaceutically acceptable carrier. The medical condition includes allergic disorders, angiogenesis, gastrointestinal disorders, CNS disorders, inflammatory diseases, emesis, urinary incontinence, pain, migraine, sunburn, and diseases, disorders and adverse conditions caused by *Helicobacter pylori* in a mammalian subject.

The present invention also provides a method for the prevention or treatment of a medical condition for which substance P receptor antagonist activity is needed, in a mammalian subject, which comprises administering to said subject a compound of the formula (I) or a pharmaceutically acceptable salt thereof.

DETAILED DESCRIPTION OF THE INVENTION

In this specification, the term "$C_1$–$C_6$ alkoxy" is used herein to mean a straight or branched —OR (R is $C_1$–$C_6$ alkyl) including, but not limited to, methoxy, ethoxy, propoxy, isopropoxy, n-butoxy, iso-butoxy, tert-butoxy and the like.

The term "halo $C_1$–$C_6$ alkyl" means a straight or branched halo alkyl of 1 to 6 carbon atoms including, but not limited to methyl, ethyl, n-propyl, iso-propyl, n-butyl, sec.-butyl and tert.-butyl, substituted by 1 to 13 (preferably 1 to 5) halogen atoms.

The term "halo" means F, Cl, Br and I, preferably Cl or F.

Preferably, $R^1$ is $C_1$–$C_3$ alkoxy such as methoxy, $C_1$–$C_3$ alkyl such as methyl or fluorinated $C_1$–$C_3$ alkyl such as trifluoromethyl.

Preferably, $R^2$ is hydrogen, $C_1$–$C_6$ (preferably $C_1$–$C_3$) alkyl, halo $C_1$–$C_6$ (preferably $C_1$–$C_3$) alkyl, $C_1$–$C_6$ (preferably $C_1$–$C_3$) alkyl-S—, $C_1$–$C_6$ (preferably $C_1$–$C_3$) alkyl-SO— or $C_1$–$C_6$ (preferably $C_1$–$C_3$) alkyl-SO$_2$—. More preferably $R^2$ is hydrogen or trifluoromethyl.

Preferably, X is NH or O.

Preferably, Y is hydrogen or —COOH at the 5-position of the quinuclidine ring.

Preferably, $Ar^1$ and $Ar^2$ are phenyl.

When X is NH, $R^1$ is preferably $C_1$–$C_3$ alkoxy at the 2-position of the phenyl ring, or $C_1$–$C_3$ alkyl or fluorinated $C_1$–$C_3$ alkyl at the 3-position of the phenyl ring. When X is O, $R^1$ is preferably $C_1$–$C_3$ alkyl or fluorinated $C_1$–$C_3$ alkyl at the 3-position of the phenyl ring.

In these compounds, preferable stereochemistry of 2-aryl and 3-substituted benzyl group is (2S,3S) or (2R, 3S), more preferably (2S,3S).

Preferred individual compounds of this invention are following:
- (2S,3S)-3-[2-methoxy-5-(5-trifluoromethyl-tetrazol-1-yl) benzylamino]-2-diphenylmethyl-1-azabicyclo[2.2.2] octane or its salts;
- (2S,3S,4S,5R)-3-[2-methoxy-5-(5-trifluoromethyl-tetrazol-1-yl)benzylamino]-2-diphenylmethyl-1-azabicyclo[2.2.2]octan-5-carboxylic acid or its salts;
- (2S,3S,4R,5S)-3-[2-methoxy-5-(5-trifluoromethyl-tetrazol-1-yl)benzylamino]-2-diphenylmethyl-1-azabicyclo[2.2.2]octan-5-carboxylic acid or its salts;
- (2S,3S)-3-[3-trifluoromethyl-5-(5-trifluoromethyl-tetrazol-1-yl) benzylamino]-2-diphenylmethyl-1-azabicyclo-[2.2.2]octane;
- (2S,3S,4S,5R)-3-[3-trifluoromethyl-5-(5-trifluoromethyl-tetrazol-1-yl)benzylamino]-2-diphenylmethyl-1-azabicyclo[2.2.2]octan-5-carboxylic acid or its salts;
- (2S,3S,4R,5S)-3-[3-trifluoromethyl-5-(5-trifluoromethyl-tetrazol-1-yl)benzylamino]-2-diphenylmethyl-1-azabicyclo[2.2.2]octan-5-carboxylic acid or its salts;
- (2S,3S)-3-[3-trifluoromethyl-5-(5-trifluoromethyl-tetrazol-1-yl)benzyloxy]-2-diphenylmethyl-1-azabicyclo-[2.2.2]octane;
- (2S,3S,4S,5R)-3-[3-trifluoromethyl-5-(5-trifluoromethyl-tetrazol-1-yl)benzyloxy]-2-diphenylmethyl-1-azabicyclo[2.2.2]octan-5-carboxylic acid or its salts; and
- (2S,3S,4R,5S)-3-[3-trifluoromethyl-5-(5-trifluoromethyl-tetrazol-1-yl)benzyloxy]-2-diphenylmethyl-1-azabicyclo[2.2.2]octan-5-carboxylic acid or its salts.

Particularly preferred compound of this invention is (2S, 3S)-3-[2-methoxy-5-(5-trifluoromethyltetrazol-1-yl-benzylamino]-2-diphenylmethyl-1-azabicyclo[2.2.2]octane or its salts.

GENERAL SYNTHESIS

The quinuclidine compounds of the formula (I) of this invention may be prepared as described in the following reaction schemes.

Unless otherwise indicated, in the reaction schemes that follow, $R^1$, $R^2$, $Ar^1$, $Ar^2$, X and Y are defined as above.

Scheme 1 illustrates a method for preparation of compounds of the formula (Ia) (i.e., X is NH in the formula (I)) by reductive amination.

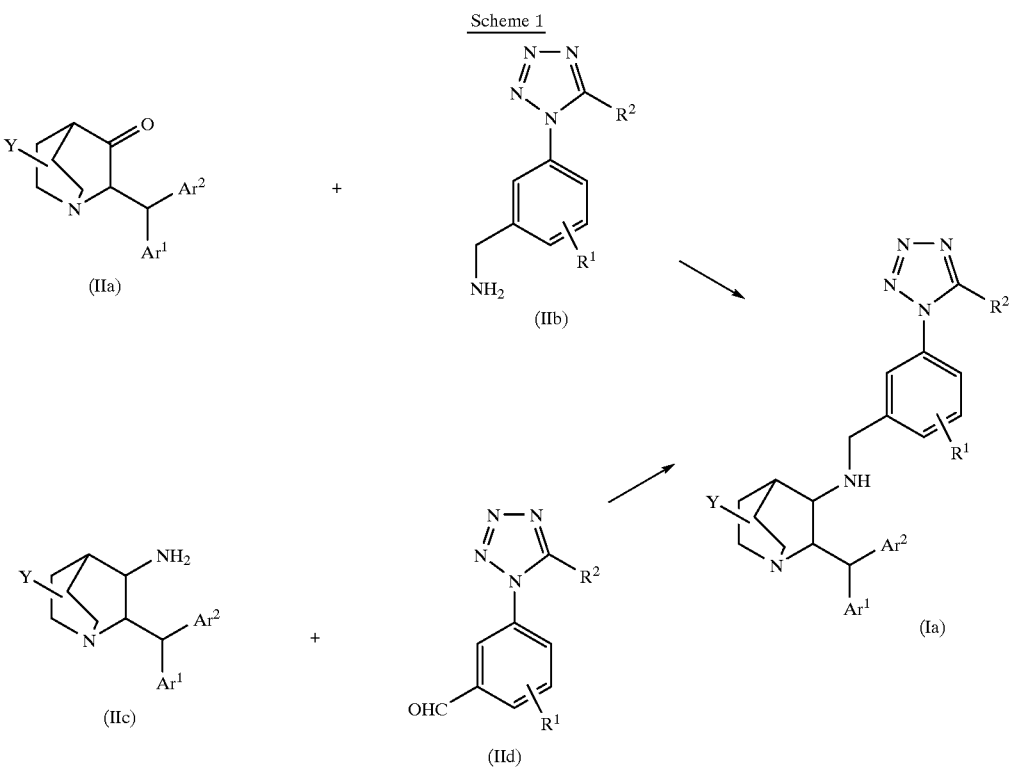

The above reductive amination of either route can be achieved by hydride-reduction or catalytic hydrogenation. For example, benzylaminoquinuclidine compounds (Ia) can be prepared by a reaction of quinuclidine-3-one (IIa) and tetrazolylbenzylamine (IIb) in the presence of a hydride agent in a reaction inert solvent. Suitable hydride agents include sodium borohyrride ($NaBH_4$), sodium cyanoborohydride ($NaBH_3CN$) and sodium acetoxyborohydride ($NaBH(OAc)_3$). Suitable solvents include methanol, ethanol, methylene chloride, acetic acid, 1,2-dichloroethane, THF and acetonitrile. This reaction can be carried out at a temperature from −78° C. to reflux temperature of the solvent, preferably from 0° C. to 25° C. for 5 minutes to 48 hours, preferably from 0.5 to 12 hours.

In some cases, this reductive amination can be also achieved by two-step reactions according to the procedures, for example, those described in WO92/20676. A compound (IIa) and compound (IIb) can be reacted to give the corresponding imine compound which is subsequently reduced to the compound (Ia) under the above condition. The imine formation can be carried out in the presence of acid catalyst such as camphor sulfonic acid (CSA) in a suitable solvent such as toluene. This reaction can be carried out at from room temperature to the reflux temperature of the solvent, preferably at reflux, for 2 to 8 hours. Then, the reduction can be carried out in the presence of a suitable hydride agent such as NaBH(OAc)$_3$. This reaction can be carried out in a suitable solvent such as methylene chloride or acetic acid, at a temperrature from 0° C. to 50° C., preferably at room temperature, for 2 to 24 hours.

Benzylaminoquinuclidine compounds of the formula (Ia) can be also prepared by condensation of 3-amino-2-diarylmethylquinuclidine (IIc) and substituted terazolylbenzaldehyde (IId), followed by reduction. These procedures are described in more detail in International Publication Nos. WO94/10170 and WO94/26740.

This condensation can be carried out in the presence of a hydride agent such as NaBH$_3$CN and NaBH(OAc)$_3$. Suitable solvents incude methylene chloride, acetonitrile, acetic acid and methanol. This reaction can be carried out at a temperature from −25° C. to reflux temperature of the solvent, preferably at room temperature, for 0.5 to 48 hours, preferably 2 to 12 hours.

In addition, the quinuclidine-3-ones (IIa) are known compounds, and may be prepared by known procedures as described in International Publications Nos. WO90/05729, WO92/20676, WO94/26740 and WO95/02595 and European Patent Publication No. EP 0,499,313A1. The 3-amino-2-diarylmethylquinuclidines (IIc) are known compounds, and may be prepared by known procedures as described in WO92/20676, WO94/10170 or WO/94/26740.

Further, the substituted tetrazolylbenzaldehydes (IId) can be prepared according to the procedures described in *Bioorganic & Medicinal Chemistry letters*, Vol. 6, No. 9. pp. 1015–1020, 1996 and WO95/08549. The substituted tetrazolylbenzaldehydes (IId) can be converted to the corresponding tetrazolylamines (IIb) according to the procedures described in WO92/20676 and WO94/26740.

Scheme 2 illustrates a method for preparation of compounds of the formula (Ib) (i.e., X is O in the formula (I)).

Scheme 2

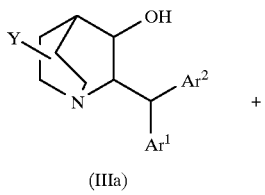

(IIIa)

+

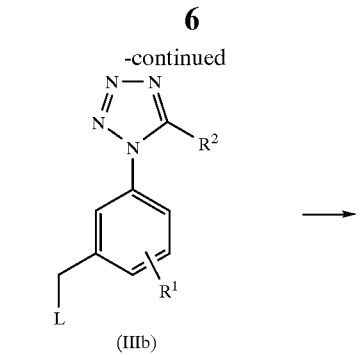

(IIIb)

L is a leaving group
(such as Cl, Br, MsO, TsO, or TfO)

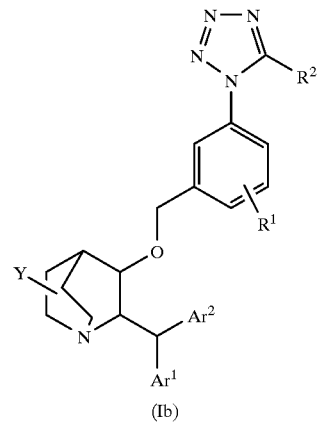

(Ib)

Benzyloxyquinuclidine compounds (Ib) can be prepared by benzylation of a compound of the formula (IIIa) in the presence of tetrazolylbenzylchloride, tetrazolylbenzylbromide, tetrazolylbenzylmethanesulfonate, tetrazolylbenzyl-p -toluenesulfonate or tetrazolylbenzyltrifluoromethanesulfonate of the formula (IIIb), according to the procedures described in WO 95/02595. This benzylation can be carried out in the presence of a base in a reaction inert solvent. Suitable base includes sodium hydride, potassium hydride, potassium t-butoxide, lithium diisopropylamide (LDA), lithium bis (trimethylsilyl)amide, sodium bis (trimethylsilyl)amide or potassium bis(trimethylsilyl)amide. Suitable solvents include ether, tetrahydrofuran (THF), dimethylether (DME) and N,N-dimethylformamiede (DMF). This reaction can be carried out at a temperature from −78° C. to reflux temperature of the solvent, preferably −5° C. to 30° C. for 30 minutes to 48 hours, preferably from 30 to 4 hours.

If necessary, the Y group may be properly protected during the above coupling reaction. The Y group in the compounds (Ia) or (Ib) may be epimerized, by known methods, to control desired stereochemistry.

In addition, the compounds of the formula (IIIa) are known compounds, and may be prepared from the corresponding substituted quinuclidine-3-one by the procedures as described in EP 0,499,313A1, WO95/02595, and *J. Med. Chem*, Vol. 17, p. 497, 1974 or *Bioorg. Med. Chem. Lett.*, Vol. 3, p. 1703, 1993.

When the compounds of the formula (I) wherein X is S is desired, such compounds can be prepared in the following manner.

Benzylthio compounds of the formula (I) wherein X is S are obtainable from quinuclidine-3-thiols by the reaction with a benzylhalide or a benzylsulfonyl compound (IIb), as described in WO 95/02595. The quinuclidine-3-thiol may be prepared from a quinuclidine-3-one or a quinuclidine-3-ol by convential procedures. For example, a quinuclidine-3-one can be converted to the corresponding quinuclidine-3-thiol via thioketal according to the procedures described in J. Am. Chem. Soc., Vol 102, pp. 3577 et seq., 1980. The quinuclidine-3-thiol can be also prepared from the quinuclidine-3-ol for example by the reaction of the corresponding mesylate with potassium thioacetate.

Scheme 3 illustrates a method for preparation of an intermediate (IIIb).

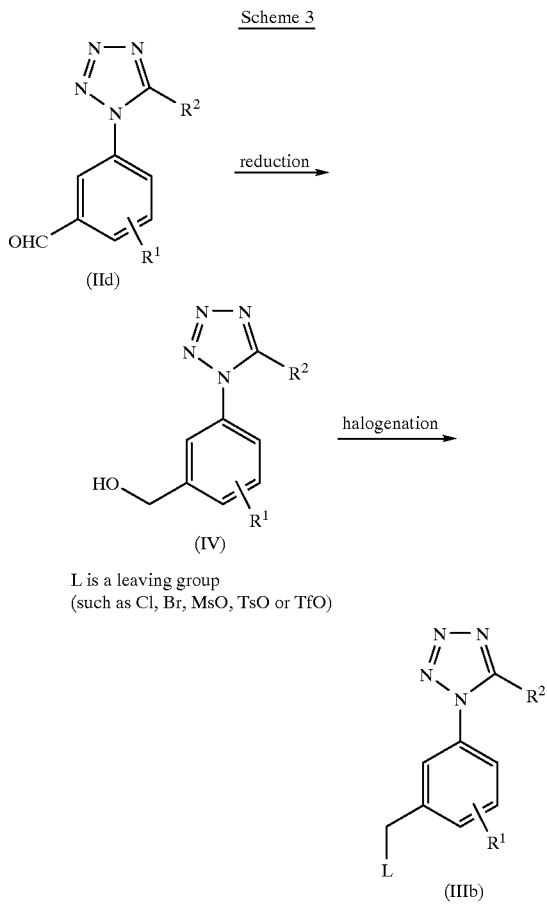

L is a leaving group
(such as Cl, Br, MsO, TsO or TfO)

Benzylchloride or benzylbromide compounds (IIIb) can be prepared by reduction of a compound (IId) to give benzylalcohol (IV), followed by halogenation. This reduction can be carried out in the presence of a reducing agent in an alcohol solvent. A preferred reducing agent is sodium borohydride. Suitable alcohol solvents include methanol and ethanol. This reaction can be carried out at a temperature from −30° C. to 30° C., for 5 minutes to 5 hours. The halogenation can be carried out by known procedures as described in EP 0,499313A1.

Corresponding benzylsulfonate compounds (IIIb) can be prepared by treatment of the benzylalcohol (IV) with a sulfonylating agent such as methanesulfonyl chloride, tosyl-chloride or triflic anhydride. This reaction is usually carried out in the presence of a base such as pyridine, triethylamine, diisopropylethylamine, N,N-dimethylaminopyridine in a proper solvent such as methylene chloride or pyridine under suitable conditions.

The compounds of formula (I), and the intermediates shown in the above reaction schemes can be isolated and purified by conventional procedures, such as recrystallization or chromatographic separation.

As the quinuclidine compounds of this invention possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

In so far as the quinuclidine compounds of this invention are basic compounds, they are all capable of forming a wide variety of different salts with various inorganic and organic acids. Although such salts must be pharmaceutically acceptable for administration to animals, it is often desirable in practice to initially isolate the quinuclidine base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acid which are used to prepare the pharmaceutically acceptable acid addition salts of the aforementioned quinuclidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts.

The quinuclidine compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques.

The chemical bases which are used as reagents to prepare the pharmaceutically acceptable base salts of this invention are those which form non-toxic base salts with the herein described acidic quinuclidine derivatives. These particular non-toxic base salts include those derived form such pharmaceutically acceptable cations as sodium, potassium, calcium and magnesium, etc. These salts can easily be prepared by treating the aforementioned acidic quinuclidine compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active quinuclidine compounds of the present invention exhibit significant substance P receptor-binding activity and therefore, are of value in the treatment of a wide variety of clinical conditions which are characterized by the presence of an excess of said substance P activity. Such conditions include gastrointestinal disorders, central nervous system disorders, inflammatory diseases, emesis, urinary incontinence, pain, migraine or angiogenesis in a mammalian subject, especially humans. For treatment of emesis, these compounds may preferably be used in combination with a $5HT_3$ receptor antagonist.

The active quinuclidine compounds of the formula (I) of this invention can be administered via either the oral, parenteral or topical routes to mammals. In general, these compounds are most desirably administered to humans in doses ranging from about 0.3 mg up to 750 mg per day, although variations will necessarily occur depending upon the weight and condition of the subject being treated and the particular route of administration chosen. However, a dosage level that is in the range of from about 0.06 mg to about 2 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipient such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in CHO-cells which reveal NK1 receptor or IM-9 cells employing radioactive reagents. The substance P antagonist activity of the herein described quinuclidine compounds is evaluated by using the standard assay procedure described by D. G. Payan et al., as reported in *The Journal of Immunology*, Vol. 133, p. 3260, 1984. This method essentially involves determining the concentration of the individual compound required to reduce by 50% the amount of radiolabelled substance P reagents at their receptor sites in said isolated cow tissues or IM-9 cells, thereby affording characteristic $IC_{50}$ values for each compound tested. More specifically, inhibition of [$^3$H]SP binding to human IM-9 cells by compounds are determined in assay buffer (50 mM Tris-HCl (pH 7.4), 1 mM $MnCl_2$, 0.02% bovine serum albumin, bacitracin (40 µg/ml), leupeptin (4 µg/ml), chymostatin (2 µg/ml) and phosphoramidon (30 µg/ml)). The reaction is initiated by the addition of cells to assay buffer containing 0.56 nM [$^3$H]SP and various concentrations of compounds (total volume; 0.5 ml) and allowed to incubate for 120 min at 4° C. Incubation is terminated by filtration onto GF/B filters (presoaked in 0.1% polyethylenimine for 2 hours). Nonspecific binding is defined as the radioactivity remaining in the presence of 1 µM SP. The filters are placed into tubes and counted using liquid scintillation counter.

Alternatively, the anti-inflammatory activity of the compounds of this invention, in the periphery of a mammalian subject, is demonstrated by a capsaicin-induced plasma extravasation test, using the procedure described by A. Nagahisa et al, as reported in *European Journal of Pharmacology*, Vol.217, pp.191–195, 1992. In this test, anti-inflammatory activity is determined as the percent inhibition of plasma protein extravasation in the ureter of pentbarbital-anesthetized (25 mg/kg i.p.) male Hartey guinea pigs (weighing 300–350 g). Plasma extravasation is induced by intraperitoneal injection of capsaicin (30 µM in 0.1 BSA containing buffer, 10 ml/animal) into the animals and fasted overnight. The compounds of this invention was dissolved in 0.1% methyl cellulose-water and given orally 1 hour before capsaicin challenge. Evans blue dye (30 mg/kg) was administered intravenously 5 minutes before challenge. The animals were killed 10 minutes after capsaicin injection and both right and left ureter were removed. Tissue dye content was quantitated after overnight formamide extraction at 600 nm absorbance. The compound, prepared in Example as described below, was tested in accordance with the above procedures, and showed good oral activities (i.e., 75% inhibition at a dose range of less than 0.02 mg/kg, p.o.).

The adverse effect on $Ca^{2+}$ channel binding affinity is determined by study of verapamil binding in a rat heart membrane preparation. More specifically, verapamil binding is performed as previously described by Reynolds et al., (*J. Pharmacol. Exp. Ther.* Vol. 237, p. 731, 1986). Briefly, incubations are initiated by the addition of tissue to tubes containing 0.25 nM [$^3$H]desmethoxyverapamil and various concentrations of compounds (total volume; 1 ml). Nonspecific binding is defined as radioligand binding remaining in the presence of 3–10 μM methoxyverapamil.

The activity of the compounds of this invention against CNS disorders is determined in a [$Sar^9$, $Met(O_2)^{11}$] substance P-induced tapping test in gerbils. More specifically, gerbils are lightly anesthetized with ether and the skull surface is exposed. [$Sar^9$, $Met(O_2)^{11}$]substance P or vehicle (5 μl) are administered directly into the lateral ventricles via a 25 gauge needle inserted 3.5 mm below lambda. Following injection, gerbils are placed in 2 liter beaker individually and monitored for repetitive hind paw tapping.

The half life of the compounds of this invention is determined in a human liver microsome preparation. More specifically, the compound (1 μM) was incubated with pooled human liver microsome (2.0 mg/ml), NADP (1.3 mM), NADH (0.93 mM), glucose-6-phosphate (3.3 mM) $MgCl_2$ (3.3 mM), and glucose-6-phosphate dehydrogenase (8 units/ml) in a total volume of 1.2 ml 100 mM potassium phosphate buffer, pH 7.4. At various time points (0, 5, 10, 30 and 60 min), a 100 μl sample was added to acetonitrile solution (1.0 ml), which included an internal standard. The precipitated protein was spun down in a centrifuge (3,000×g, 5 min). The supernatant w as analyzed by LC-MS. LC-MS unit was consisted of Hewlett Packard HP1090 HPLC system and Sciex API-III. Samples(10 μl) were injected by means of autosampler, onto Hewlett Packard ODS-Hypersil column (2.1×20 mm). A mobile phase was consisted of 80% acetonitrile in 10 mM ammonium acetate. The measurement of API-III was analyzed with multiple reacting monitoring (MRM) detection.

EXAMPLE

The present invention is illustrated by the following example. However, it should be understood that the invention is not limited to the specific details of the example. Melting points were taken with a Buchi micro melting point apparatus and uncorrected. Infrared Ray absorption spectra (IR) were measured by a Shimadzu infrared spectrometer (IR-470). $^1$H nuclear magnetic resonance spectra (NMR) was measured in $CDCl_3$ by a JEOL NMR spectrometer (JNM-GX270, 270 MHz for $^1$H) unless otherwise indicated and peak positions are expressed in parts per million (ppm) downfield from tetramethylsilane. The peak shapes are denoted as follows: s, singlet; d, doublet; t, triplet; m, multiplet.

Example 1

(2S,3S-3-[2-methoxy-5-(5-trifluoromethyltetrazol-1-yl) benzylamino]-2-diphenylmethyl -1-azabicyclo[2.2.2] octane

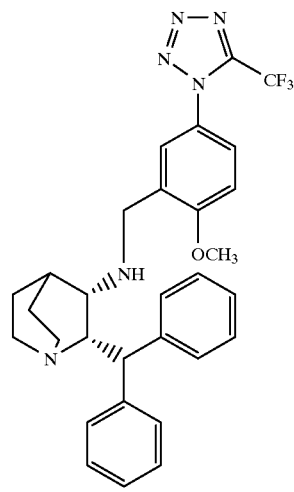

To a stirred solution of (2S,3S)-2-diphenylmethyl-1-azabicyclo[2.2.2]octane-3-amine (100 mg, 0.34 mmol) and 2-methoxy-5-(5-trifluoromethyltetrazol-1-yl)benzaldehyde (102 mg, 0.38 mmol) in anhydrous methylene chloride (4 mL) was added sodium triacetoxyborohydride (101 mg, 0.48 mmol) and acetic acid (21 mg, 0.34 mmol) portionwise under nitrogen at rt. The reaction mixture was stirred at rt. for 17 hr. This was basified with sat. $NaHCO_3$ aq., extracted with methylene chloride, dried over $MgSO_4$, and concentrated. The crude product was crystallized from isopropylalcohol to afford the title compound as a white crystalline (119 mg, 63.8%).

m.p. 158–161° C.

$^1$H-NMR ($CDCl_3$): 7.30–7.16 (m, 7H), 7.14–7.02 (m, 3H), 6.89–6.84 (m, 2H), 6.55 (d, J=2.9 Hz, 1H), 4.42 (d, J=12.5 Hz, 1H), 3.73 (s, 3H), 3.71–3.68 (m, 1H), 3.67 (d, J=14.7 Hz, 1H), 3.39 (d, J=14.7 Hz, 1H), 3.24–3.13 (m, 1H), 2.89 (dd, J=7.7, 4.0 Hz, 1H), 2.79–2.74 (m, 2H), 2.67–2.58 (m, 1H), 2.00 (br.s, 1H), 1.90–1.80 (m, 1H), 1.69–1.56 (m, 2H), 1.33–1.22 (m, 1H)

IR (KBr): 2,956, 2,863, 1,502, 1,466, 1,449, 1,250, 1,215, 1,180, 1,156, 1,037, 1,022, 755, 702 $cm^{-1}$

I claim:

1. A compound of the formula (I):

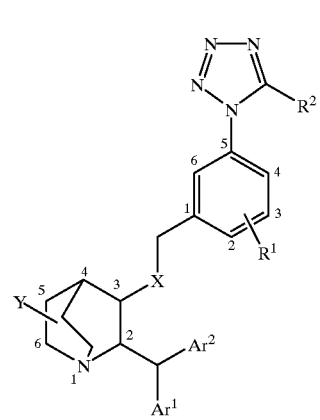

and its pharmaceutically acceptable salts, wherein
$R^1$ is halo, $C_1$–$C_6$ alkyl, halo $C_1$–$C_6$ alkyl, $C_1$–$C_6$ alkoxy or halo $C_1$–$C_6$ alkoxy;
$R^2$ is hydrogen, $C_1$–$C_6$ alkyl, halo $C_1$–$C_6$ alkyl, $C_1$–$C_6$ alkyl-S—, $C_1$–$C_6$ alkyl-SO—, $C_1$–$C_6$ alkyl-$SO_2$—, cyclopropyl, phenyl, —NH$_2$, —NH(CH$_3$), —NHC(=O)CH$_3$, —N(CH$_3$)$_2$, —N(C$_2$H$_5$)$_2$ or —CH$_2$C(=O)CF$_3$;

Ar$^1$ and Ar$^2$ are independently phenyl, halophenyl or thienyl;

X is NH, O or S; and

Y is hydrogen, —COOR$^3$ or —CONR$^4$R$^5$, wherein R$^3$, R$^4$ and R$^5$ are independently hydrogen or C$_1$–C$_6$ alkyl.

2. A compound according to claim 1, wherein R$^2$ is hydrogen, C$_1$–C$_6$ alkyl, halo C$_1$–C$_6$ alkyl, C$_1$–C$_6$ alkyl-S-, C$_1$–C$_6$ alkyl-SO— or C$_1$–C$_6$ alkyl-SO$_2$—.

3. A compound according to claim 2, wherein

R$^2$ is hydrogen or trifluoromethyl;

X is NH or O;

Y is hydrogen or —COOH at the 5-position on the quinuclidine ring; and

Ar$^1$ and Ar$^2$ are phenyl.

4. A compound according to claim 3, wherein X is NH; and R$^1$ is C$_1$–C$_3$ alkoxy at the 2-position of the phenyl ring, or C$_1$–C$_3$ alkyl or fluorinated C$_1$–C$_3$ alkyl at the 3-position on the phenyl ring.

5. A compound according to claim 4, wherein R$^1$ is methoxy.

6. A compound according to claim 5 selected from (2S,3S)-3-[2-methoxy-5-(5-trifluoromethyl-tetrazol-1-yl)benzylamino]-2-diphenylmethyl-1-azabicyclo[2.2.2]octane or its salts;

(2S,3S,4S,5R)-3-[2-methoxy-5-(5-trifluoromethyl-tetrazol-1-yl)benzylamino]-2-diphenylmethyl-1-azabicyclo[2.2.2]octan-5-carboxylic acid or its salts; and (2S,3S,4R,5S)-3-[2-methoxy-5-(5-trifluoromethyl-tetrazol-1-yl)benzylamino]-2-diphenylmethyl-1-azabicyclo[2.2.2]octan-5-carboxylic acid or its salts.

7. A compound according to claim 6, which is (2S,3S)-3-[2-methoxy-5-(5-trifluoromethyltetrazol-1-yl)benzylamino]-2-diphenylmethyl-1-azabicyclo[2.2.2]octane or its salts.

8. A compound according to claim 4 selected from (2S,3S)-3-[3-trifluoromethyl-5-(5-trifluoromethyl-tetrazol-1-yl)benzylamino]-2-diphenylmethyl-1-azabicyclo[2.2.2]octane;

(2S,3S,4S,5R)-3-[3-trifluoromethyl-5-(5-trifluoromethyl-tetrazol-1-yl)benzylamino]-2-diphenylmethyl-1-azabicyclo[2.2.2]octan-5-carboxylic acid or its salts; and (2S,3S,4R,5S)-3-[3-trifluoromethyl-5-(5-trifluoromethyl-tetrazol-1-yl)benzylamino]-2-diphenylmethyl-1-azabicyclo[2.2.2]octan-5-carboxylic acid or its salts.

9. A compound according to claim 3, wherein X is O; and R$^1$ is C$_1$–C$_3$ alkyl or fluorinated C$_1$–C$_3$ alkyl at the 3-position at the phenyl ring.

10. A compound according to claim 9, wherein R$^1$ is methyl or trifluoromethyl.

11. A compound according to claim 10 selected from (2S,3S)-3-[3-trifluoromethyl-5-(5-trifluoromethyl-tetrazol-1-yl)benzyloxy]-2-diphenylmethyl-1-azabicyclo-[2.2.2]octane;

(2S,3S,4S,5R)-3-[3-trifluoromethyl-5-(5-trifluoromethyl-tetrazol-1-yl)benzyloxy]-2-diphenylmethyl-1-azabicyclo[2.2.2]octan-5-carboxylic acid or its salts; and (2S,3S,4R,5S)-3-[3-trifluoromethyl-5-(5-trifluoromethyl-tetrazol-1-yl)benzyloxy]-2-diphenylmethyl-1-azabicyclo[2.2.2]octan-5-carboxylic acid or its salts.

12. A pharmaceutical composition for the treatment of a medical condition for which substance P receptor antagonist activity is needed, in a mammalian subject, which comprises a therapeutically effective amount of a compound according to claim 1 or a pharmaceutically acceptable salt thereof, and a pharmaceutically acceptable carrier.

13. A pharmaceutical composition according to claim 12, the medical condition is selected from allergic disorders, angiogenesis, gastrointestinal disorders, central nervous system disorders, inflammatory diseases, emesis, urinary incontinence, pain, migraine, sunburn, and diseases, disorders and adverse conditions caused by *Helicobacter pylori* in a mammalian subject.

14. A method for the treatment of a medical condition in a mammalian subject for which substance P receptor antagonist activity is needed, which comprises administering to said subject a therapeutically effective amount of a compound according to claim 1 or a pharmaceutically acceptable salt thereof.

15. A method according to claim 14, the medical condition is selected from allergic disorders, angiogenesis, gastrointestinal disorders, central nervous system disorders, inflammatory diseases, emesis, urinary incontinence, pain, migraine, sunburn, and diseases, disorders and adverse conditions caused by *Helicobacter pylori* in a mammalian subject.

* * * * *